United States Patent [19]

Appleby

[11] Patent Number: 4,897,037
[45] Date of Patent: Jan. 30, 1990

[54] DENTAL BUR

[76] Inventor: David C. Appleby, 239 Chestnut St., Haddonfield, N.J. 08033

[21] Appl. No.: 281,168

[22] Filed: Dec. 8, 1988

[51] Int. Cl.⁴ ............................................... A61C 3/06
[52] U.S. Cl. ..................................... 433/166; 433/75; 40/913
[58] Field of Search ............... 433/166, 165, 142, 102, 433/75; 40/913

[56] References Cited

U.S. PATENT DOCUMENTS

| | | | |
|---|---|---|---|
| 959,054 | 5/1910 | Glover | 433/166 |
| 2,092,689 | 9/1937 | Austin | 433/116 |
| 2,807,264 | 9/1957 | Tuck | 433/166 |
| 3,935,640 | 2/1976 | Cohan | 433/75 |
| 4,231,738 | 11/1980 | Riitano et al. | 433/102 |
| 4,527,449 | 7/1985 | Sydlowski et al. | 76/108 R |

Primary Examiner—John J. Wilson
Attorney, Agent, or Firm—Norman E. Lehrer

[57] ABSTRACT

A dental bur includes a shank adapted to be held by a dental drill and an abrasive portion. The lowermost abrasive portion at the free end of the bur is of a different color from the remaining abrasive portion. As a result, a dentist can observe the colored section to determine the depth of the bur tip under the gum line. Preferably, the bur is formed by coloring the corresponding section of the substrate from which the bur is made and then coating the entire working surface of the bur (colored and uncolored) with diamond chips.

12 Claims, 1 Drawing Sheet

DENTAL BUR

BACKGROUND OF THE INVENTION

The present invention is directed toward a dental bur and more particularly toward such a bur which is useful in the preparation of a tooth for restoration.

Dental burs of various sizes and shapes have been known and used for many years. The majority of these burs are comprised of axially extending steel bits which are coated on the working surfaces thereof with abrading material such as industrial diamond chips. An uncoated shank portion is held in a dental drill.

Burs of this type are often employed to remove enamel and dentin from a tooth in order to prepare the same for the placement of a restoration. Such restorations may be comprised of metal, plastic, quartz, porcelain or a variety of other materials or combinations thereof.

Occasionally a tooth is so broken down by decay or trauma that it must be reinforced by surrounding the entire tooth with the restoration material. The sides and chewing surfaces of the tooth are removed with the diamond burs so that there is space for the restoration or replacement. Restorations of this type are normally referred to as "crowns" since they replace the anatomical crown of the tooth with its size and shape duplicating the contours of the original enamel crown.

Crowns for front teeth are frequently made from tooth-colored material such as porcelain or porcelain-coated metal so as to look natural. As the sides of the tooth are being reduced in order to prepare the same for a crown, the tip of the diamond bur must be placed under the gum line. This is done for aesthetic purposes to ensure that the crown will end under the gum where no one can see it. In other words, the line of transition between drilled and undrilled tooth, known as the finish line, is placed subgingivally or under the gum line.

The subgingival distance at which a finish line should be placed is dependent upon the biological dictates and aesthetic requirements of the patient. Let us suppose, for example, that the dentist wishes to place the finish line 1 mm subgingivally. However, as the elongated bur is turning, there is no way to be certain how deep the bur has been placed subgingivally because known prior art burs are of a uniform color throughout the length of the working surface thereof. While Applicant is familiar only with burs having a uniform silver or black color, it is believed that burs have been proposed in the past having uniform colors other than silver or black.

Since a dentist has no way of being certain as to how deep the bur has been placed, the finish line may be uneven or ragged which can result in the improper fitting of a crown. To Applicant's knowledge, no one has ever proposed a dental bur which is particularly adapted to guide a dentist in the preparation of a subgingival finish line. In fact, Applicant is not aware of any previously proposed solution to this problem nor even the recognition of the same by others.

SUMMARY OF THE INVENTION

The present invention is designed to overcome the problems of the prior art described above. The dental bur according to the invention includes a shank which is adapted to be held by a dental drill and also includes an abrasive portion. The lowermost section of the abrasive portion at the free end of the bur is of a different color from the remaining abrasive portion. In use, only a part of the colored section is placed subgingivally so that the dentist can observe the remaining part of the colored section as he is working in order to maintain the depth of the bur at the proper level.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE PREFERRED EMBODIMENT

Figure 1:
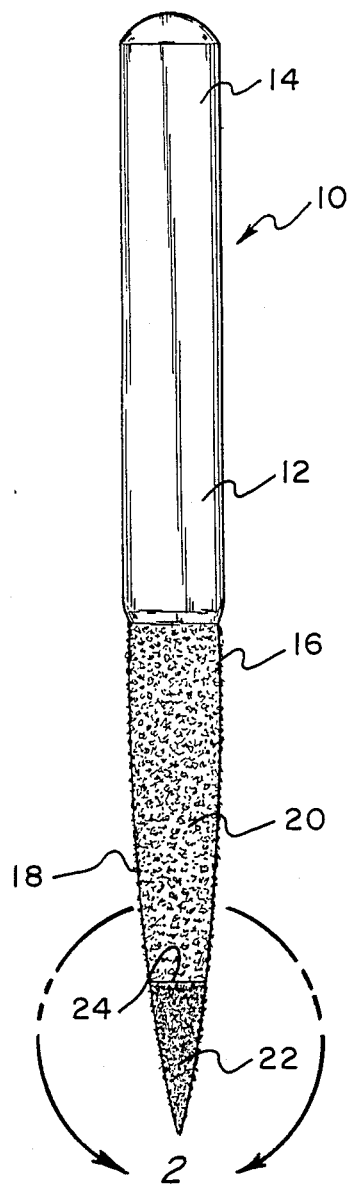
FIG. 1 is an enlarged elevational view of a dental bur constructed in accordance with the principles of the present invention.

Referring now to the drawing in detail wherein like reference numerals have been used in both figures to designate like elements, there is shown in FIG. 1 a dental bur constructed in accordance with the principles of the present invention and designated generally as 10. Bur 10 is formed of an axially extending stainless steel substrate 12 which has a nonabrasive shank portion forming the upper part thereof. This shank portion is held by the dental drill. The lower portion 16 of the dental bur 10 is the abrading portion which is connected to and extends downwardly from the shank portion 14.

Figure 2:
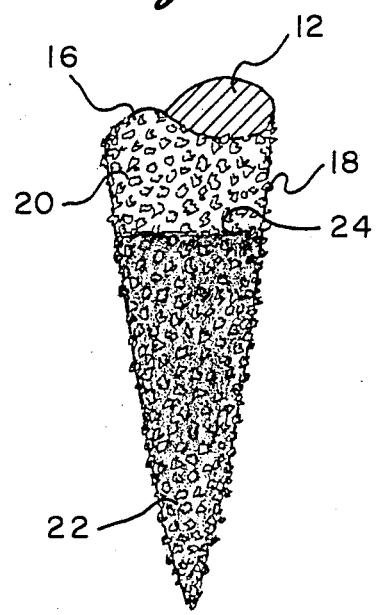
FIG. 2 is a further enlarged view of the lower portion of FIG. 1.

As is well known in the art, the abrading portion 16 is formed by electroplating diamond chips 18 or other abrasive particles onto the substrate from which the bur is formed. This process per se is well known. In fact, the dental bur so far described is one form of a conventional dental bur well known in the art. The improvement of the present invention is shown in the lowermost portion of the dental bur of FIG. 1 and in the enlargement thereof shown in FIG. 2.

The abrasive portion 16 of the dental bur 10 is divided into two distinct and axially separate sections 20 and 22. These two sections have significantly different optical appearances from each other and there is a clear line of demarcation 24 between the two sections. For example, the upper section 20 may be a light shade while the lower section 22 may be a dark shade or they may be fabricated so as to be of different colors. One of the sections may be white while the other is black or of substantially any other color. Of course, it would not be desirable to utilize red as a color since the preparation of subgingival finish lines frequently causes gums to bleed and the red color of the blood might interfere with the use of the bur.

In the preferred embodiment of the invention, the length of the lowermost section 22 of the bur 10 is 2 mm. Thus, when the device is being used to create a subgingival finish line of 1 mm, the dentist merely has to watch the demarcation line 24 between the two different colored portions to ensure that the same remains approximately 1 mm above the gum line.

One method of forming the two different colors for the abrasive sections 20 and 22 is to electroplate two differently colored abrasive particles onto the substrate 12. This can be accomplished by first covering one of the sections with a resist or insulating material while electroplating the other section and then reversing the procedure, i.e. covering the section already plated while electroplating the unplated section with a differently colored abrasive particle material.

A preferred form of fabricating the abrasive sections, however, is to color the substrate rather than using differently colored abrasive particles. This can be accomplished by either electroplating a material onto the entire substrate or oxidizing the same in order to form a distinctive color thereon. The color can then be removed from either section 20 or 22 by grinding or otherwise abrading the same. Thereafter, diamond chips or similar abrasive particles which are substantially translucent or transparent can then be electroplated onto the abrasive portion 16 in a known manner. The color differences between sections 20 and 22 and the line of demarcation 24 will then clearly be seen through the diamond chips.

The shape of the dental bur 10 shown in FIG. 1 is, of course, by way of example only. Finish lines can be prepared in several different shapes including a bevel, a slope (commonly referred to as a chamfer) and a right angled butt joint (called a shoulder). Each of these is made with a differently shaped bur which is specifically designed for the desired result. Similarly, burs of the same shape may come in multiple lengths and widths. The type of crown to be fabricated, the size and shape of the tooth and the biological demands of the environment all dictate the shape of the finish line which, in turn, dictates the size and shape of the bur chosen to prepare that finish line. Thus, the concept of the present invention can be adapted to all types of burs that could be used to place subgingival finish lines.

The present invention may be embodied in other specific forms without departing from the spirit or essential attributes thereof and accordingly reference should be made to the appended claims rather than to the foregoing specification as indicating the scope of the invention.

I claim:

1. A dental bur comprising:
   a nonabrasive shank portion adapted to be held by a dental drill;
   an abrading portion connected to and extending downwardly from said shank portion;
   said abrading portion having substantially the same abrading properties throughout the length thereof but being divided into two distinct, axially separate and differently colored sections.

2. The invention as claimed in claim 1 wherein said abrading portion is formed of a substrate and abrasive particles adhered to said substrate.

3. The inventio,n as claimed in claim 2 wherein said differently colored abrading sections is caused by said substrate being divided into two sections having different colors.

4. The invention as claimed in claim 3 wherein said abrasive particles are at least substantially translucent.

5. The invention as claimed in claim 3 wherein the two different colors of said substrate sections are formed by oxidizing the surface of one of said sections.

6. The invention as claimed in claim 4 wherein the two different colors of said substrate sections are formed by oxidizing the surface of said substrate and thereafter removing the oxidation from the surface of one of said sections.

7. A dental bur comprising:
   a nonabrasive shank portion adapted to be held by a dental drill;
   an abrading portion connected to and extending downwardly from said shank portion;
   said abrading portion having substantially the same abrading properties throughout the length thereof but being divided into two distinct, axially separtate and differently shaded sections.

8. The invention as claimed in claim 7 wherein said abrading portion is formed of a substrate and abrasive particles adhered to said substrate.

9. The invention as claimed in claim 8 wherein said differently shaded abrading sections is caused by said substrate being divided into two sections having different shades.

10. The invention as claimed in claim 9 wherein said abrasive particles are at least substantially translucent.

11. The invention as claimed in claim 9 wherein the two different shades of said substrate sections are formed by oxidizing the surface of one of said sections.

12. The invention as claimed in claim 9 wherein the two different shades of said substrate sections are formed by oxidizing the surface of said substrate and thereafter removing the oxidation from the surface of one of said sections.

* * * * *